United States Patent
Arnold et al.

(10) Patent No.: US 9,545,291 B2
(45) Date of Patent: Jan. 17, 2017

(54) DENTAL IMPLANT

(75) Inventors: Peter Arnold, Hexham (GB); Daniel Sarefjord, Stochholm (SE); Andrew Thompson, York (GB)

(73) Assignee: Smith & Nephew plc, London (GB)

( * ) Notice: Subject to any disclaimer, the term of this patent is extended or adjusted under 35 U.S.C. 154(b) by 1641 days.

(21) Appl. No.: 12/596,146

(22) PCT Filed: Apr. 15, 2008

(86) PCT No.: PCT/GB2008/001317
§ 371 (c)(1),
(2), (4) Date: Dec. 16, 2010

(87) PCT Pub. No.: WO2008/125852
PCT Pub. Date: Oct. 23, 2008

(65) Prior Publication Data
US 2011/0111368 A1    May 12, 2011

(30) Foreign Application Priority Data
Apr. 17, 2007    (GB) .................................. 0707418.0

(51) Int. Cl.
*A61C 8/00* (2006.01)
*A61C 13/30* (2006.01)

(52) U.S. Cl.
CPC ........... *A61C 8/0012* (2013.01); *A61C 8/0033* (2013.01); *A61C 13/30* (2013.01); *A61C 2201/007* (2013.01)

(58) Field of Classification Search
CPC ... A61C 8/0018; A61C 8/0016; A61C 8/0012; A61C 8/0033; A61C 13/30; A61C 2201/007
USPC ........ 433/172–177, 201.1, 220, 225; 606/78, 606/310, 313, 331; 411/909, 913
See application file for complete search history.

(56) References Cited

U.S. PATENT DOCUMENTS

| | | | |
|---|---|---|---|
| 3,856,905 A | 12/1974 | Dawson | |
| 3,926,459 A | 12/1975 | Pontigny | |
| 4,950,258 A | 8/1990 | Kawai et al. | |
| 5,108,289 A | 4/1992 | Fukuyo | |
| 5,951,288 A | 9/1999 | Sawa | |
| 6,160,084 A | 12/2000 | Langer et al. | |
| 6,277,390 B1 | 8/2001 | Schaffner | |
| 6,281,262 B1 | 8/2001 | Shikinami | |
| 6,299,448 B1 | 10/2001 | Zdrahala et al. | |
| 7,850,717 B2 * | 12/2010 | Dewey et al. ................ | 606/246 |
| 2004/0030341 A1 | 2/2004 | Aeschlimann et al. | |

(Continued)

FOREIGN PATENT DOCUMENTS

| | | |
|---|---|---|
| DE | 1604403 B1 | 11/1970 |
| DE | 3036611 A1 | 6/1982 |

(Continued)

OTHER PUBLICATIONS

English language machine translation of FR2863479, Jun. 17, 2005.*

(Continued)

*Primary Examiner* — Heidi M Eide
(74) *Attorney, Agent, or Firm* — Taft Stettinius & Hollister LLP

(57) ABSTRACT

An implantable dental device comprising polymeric shape memory material for implantation into a cavity within alveolar bone of the jaw or within the root canal space of a tooth.

32 Claims, 25 Drawing Sheets

(56) References Cited

U.S. PATENT DOCUMENTS

| | | | |
|---|---|---|---|
| 2005/0043757 A1* | 2/2005 | Arad et al. | 606/200 |
| 2007/0083205 A1 | 4/2007 | Attawia et al. | |
| 2009/0149856 A1 | 6/2009 | Paakinaho et al. | |

FOREIGN PATENT DOCUMENTS

| | | |
|---|---|---|
| DE | 102005032005 | 1/2007 |
| DE | 102005032005 A1 | 1/2007 |
| EP | 1000958 A1 | 5/2000 |
| FR | 2863478 | 6/2005 |
| FR | 2863478 A1 | 6/2005 |
| FR | 2863479 A1 * | 6/2005 |
| GB | 1416575 A | 12/1975 |
| JP | 09234241 A | 9/1997 |
| WO | 9622061 A1 | 7/1996 |
| WO | WO9622061 | 7/1996 |
| WO | 2008131197 A1 | 10/2008 |
| WO | WO2008131197 | 10/2008 |

OTHER PUBLICATIONS

English language machine translation of FR2863478, Jun. 17, 2005.*

Lendlein, et al. "Shape-Memory Polymers." Angew. Chem. Int. Ed., (2002), 41: 2034-2057.*

International Search Report mailed Aug. 7, 2009, which was received in a corresponding application No. PCT/US2008/060821, 11 pages.

English Computer Translation for JP 09-234241 "Orthosis Having Thermally Deforming Property" Shimadzu Corp., 1 page.

Nulend, et al., "Increased Calcification of Growth Plate Cartilage as a Result of Compressive Force in Vitro," Arthritis & Rheumatism, 29(8):1002-1009(1986), 13 pages.

Nulend, et al., "Inhibition of Osteoclastic Bone Resorption by Mechanical Stimulation in Vitro," Arthritis & Rheumatism, 33(1):66-72 (1999), 11 pages.

International Preliminary Report on Patentability mailed Oct. 20, 2009, which was received in corresponding application No. PCT/US2008/060821, 9 pages.

English Patent Abstract of DE 102005032005 from esp@cenet, Publication Date Jan. 11, 2007.

Shen, et al., "Irradiation of Chemically Crosslinked Ultrahigh Molecular Weight Polyethylene," Journal of Polymer Science: Part B: Polymer Physics, vol. 34, 1063-1077 (1996), 15 pages.

Narkis, et al., "Some Properties of Silane-Grafted Moisture-Cross-linked Polyethylene," Polymer Engineering and Science, Sep. 1985, vol. 25, No. 13, 6 pages.

Gugumus, "Possibilities and limits of synergism with light stabilizers in polyolefins 2. UV absorbers in polyolefins," Polymer Degradation and Stability 75 (2002) 309-320, 12 pages.

Costa, et al., "Mechanisms of Crosslinking, Oxidative Degradation and Stabilization of UHMWPE," UHMWPE Biomaterials Handbook, Chapter 21, Copyright 2009, 15 pages.

Al-Malaika, et al., "Processing Effects on Antioxidant Transformation and Solutions to the Problem of Antioxidant Migration," Advances in Chemistry, American Chemical Society: Washington, DC, May 5, 1996, 15 pages.

English Patent Abstract of FR 2863478 from esp@cenet, published Jun. 17, 2005, 1 page.

Nulend, et al., 'Increased Calcification of Growth Plate Cartilage as a Result of Compressive Force in Vitro,' *Arthritis & Rheumatism*, 29(8):1002-1009 (1986).

Nulend, et al., 'Inhibition of Osteoclastic Bone Resorption by Mechanical Stimulation in Vitro,' *Arthritis & Rheumatism*, 33(1):66-72 (1999).

Canadian Office Action; Canadian Application No. 2,684,833; Oct. 29, 2014; 2 pages.

Canadian Office Action; Canadian Patent Application No. 2,684,833; Dec. 20, 2013; 3 pages.

First Australian Office Action; Australian Patent Office; Australian Patent Application No. 2014202458; Mar. 13, 2015; 3 pages.

* cited by examiner

DENTAL IMPLANT

CROSS REFERENCE TO RELATED APPLICATIONS

This application is the U.S. national phase of International Application No. PCT/GB2008/001317 filed on Apr. 15, 2008 and published in English on Oct. 23, 2008 as International Publication No. WO 2008/125852 A1, which application claims priority to Great Britain Application No. 07074180.0 filed on Apr. 17, 2007, the entire contents of both of which are incorporated herein by reference.

FIELD

The present invention relates to an implantable dental device comprising polymeric shape memory material for implantation into a cavity within alveolar bone of the jaw or within the root canal space of a tooth.

BACKGROUND

In restorative dentistry, implantable dental devices are used to achieve reinforcement of damaged or diseased teeth and permanent replacement of missing teeth that may have been lost or need to be replaced due to trauma, decay or disease. Dental implants can be implanted into the root canal space of a tooth to reinforce existing tooth structure and can be implanted into the root canal space of a tooth or a cavity within alveolar bone to provide means for fixation of a dental prosthesis such as a crown or bridge.

An implantable dental fixation device typically comprises an artificial root structure which is implanted into alveolar bone of the jaw or root canal space of a tooth and an abutment to allow for attachment of a dental prosthesis such as a crown or bridge.

The majority of known intraosseous dental fixation devices are cylindrical or screw-shaped devices formed from titanium or a titanium-based alloy, which can be inserted into a pre-drilled hole in the alveolar bone of the jaw. Such devices are generally designed with the aim of achieving stable long-term fixation within alveolar bone, preferably enhanced by osseointegration. Osseointegration is a process in which a direct structural and functional connection is formed between living bone and the surface of an artificial implant. Osseointegration allows implant integration with surrounding bone by means of osteoblasts growing on the surface of the device. However, osseointegration takes time and cannot be relied upon as the sole means for implant fixation. A means of providing fixation immediately on implantation is also required.

Implantable dental devices for implantation into the root canal space of a tooth are known as dental posts. Dental posts are rod-like devices that are positioned and fixated within the root canal space of a damaged tooth to reinforce compromised structural integrity of the tooth. Dental posts can also comprise an abutment to provide means from attachment of a dental prosthesis. The choice of dental post to be used depends on a number of issues including the type of damaged tooth. In this regard, different tooth types have different root numbers and configurations requiring different post configurations. In addition the type of surgical procedure, for example root canal surgery or tooth reconstruction following trauma, influences the choice of dental post. Similar to implantable fixation devices for implantation into alveolar bone, the majority of known dental posts are cylindrical devices formed from titanium or a titanium-based alloy, which can be inserted into a pre-prepared drilled hole in a root canal of a tooth.

Problems associated with known dental implants include inadequate instant and long-term fixation, implant rejection, poor aesthetics and a need for complex and repetitive surgical procedures.

Known implants are produced in a range of sizes, and dimensions. The choice of implant is dependent on a number of issues including the desired location, avoidance of integral tissue structures and the quality of the bone or dental tissue in which the implant is to be implanted. Incorrect choice of implant dimensions, including geometry and thread size in screw-type implants can accentuate insufficient or excessive mechanical loading which can lead to implant loosening and failure. Implant failure necessitates implant removal and repetitive surgical procedures.

It is imperative that a good seal is formed between an implant and an implantation cavity. A seal can be produced by use of cements or fillers or by tailoring geometry of an implant, for example providing a tapered head to a screw-type implant. However, despite use of these techniques, it can be difficult for a thorough seal to be achieved. A substandard seal can allow entry of bacteria and lead to infection of underlying bone or dental tissue. If infection occurs, implant removal may be necessary. A substandard seal may also allow entry into the implantation cavity of soft tissue, which can lead to fibrous tissue formation. This can contribute to implant failure, for example by preventing osseointegration.

Often a desired site of implantation will comprise poor quality bone or dental tissue and it is well known that fixation of an implant in poor quality tissue is likely to be poor. There are also situations where the bone or dental tissue present is of good quality, but limited in quantity. Fixation is likely to be poor if the quantity of bone or dental tissue present is limited. Generally, if initial fixation of an implant is insufficient, as tested by standard dental techniques such as load application or acoustic tests, a temporary cap is placed over the implant for as long as is necessary to achieve adequate integration and fixation of the implant, for example by osseointegration, before any further work can be carried out. This can take as long as six months.

Moreover, although pure titanium implants have good corrosion resistance and strength characteristics, their use can cause undesirable greying of gums and crown materials. Implants formed of titanium alloys can also cause problems due to the galvanic difference of the metals which can lead to corrosion, implant loosening and failure.

Known dental implants require the use of an invasive surgical technique. Traditionally, dental practitioners drill a hole in the jaw bone or root canal of a tooth, the size of which is determined by the chosen implant to be inserted or screwed in. This invasive procedure can cause damage to surrounding tissue which can affect fixation of the implant.

Dental implantation techniques and implant devices have been developed which seek to address the problems discussed above. One such technique is the use of liquefied cements to achieve enhanced dental fixation. The use of a liquefied cement, however, necessitates a multi-step, multi-component implantation procedure involving drilling of a hole of the required size to make room for the dental implant, cleaning of the whole, positioning of a dental implant in the hole and subsequent fixation in place by a dental cement.

Shape memory alloys such as Ni—Ti alloys have been suggested as enhanced fixation materials for forming dental implants. These materials, upon induction with heat, are able to expand to a pre-configured shape enabling enhanced implant fixation. U.S. Pat. No. 5,108,289 discloses a dental endosseous implant comprising a thermal shape memory material, specifically a Cu—Zn—Al or Ti—Ni alloy. The dental implant, once inserted in the bone and upon induction with heat, changes shape to seek enhanced fixation within the alveolar bone. U.S. Pat. No. 5,951,288 discloses an implant containing three separate components, a root portion, a neck portion and an abutment. The root portion consists of three legs comprising a shape memory alloys (Ni—Ti, Ti—Pd or Ti—Pd—Co alloy) which upon induction with heat separate to provide fixation of the implant.

The use of shape memory alloys seeks to provide enhanced fixation and enhanced integration by exertion of a compressive force on the surrounding bone. Compressive forces have been shown to stimulate biological processes including osseointegration ('Increased calcification of the growth plate cartilage as a result of compressive force in-vitro' Nulend et al. *Arthritis & Rheumatism*, Vol. 29 (8), 1002-1009, 1986; 'Inhibition of osteoclastic bone resorption by mechanical stimulation In Vitro' Nulend et al. *Arthritis & Rheumatism*, Vol. 33 (1), 66-72, 1999).

However, shape memory alloys are expensive. Furthermore, the use of shape memory alloys in dental implants can lead to problems associated with non-degradability and a lack of biocompatibility. For example, alloys containing nickel can initiate an allergic response in some people.

Shape memory polymers are known and have been described in U.S. Pat. No. 4,950,258 and U.S. Pat. No. 6,281,262 for use in medical devices such as tissue suture devices, blood vessel expanders, tendon and bone fixation devices.

Shape memory polymers have had very limited use in the dentistry field. U.S. Pat. No. 6,299,448 discloses a multi-component device for implanting into gums or alveolar bone which can be used to provide support for subsequent implants. Implantation of this device requires a multi-step, multi-component process. The device comprises a stent-like anchor formed from a coil, helix, mesh or tube of a shape memory material. The stent-like anchor, which defines an internal cavity, is covered by a porous sleeve. The stent-like anchor and the sleeve together form a stent assembly which is implanted to line an alveolar cavity. Once the stent assembly has been implanted, in order to activate the shape memory material and to provide the implanted device with internal structure, it is necessary for a polymerisable material to be injected into the central cavity defined by the stent assembly. Exothermic polymerisation of the polymerisable material generates heat sufficient to activate the shape memory material.

SUMMARY

There is a need in the art for an improved dental implant which addresses the problems set out above by providing enhanced instant and long-term fixation, enhanced long-term integration and an enhanced seal between the implant and the implantation cavity. Moreover, there is a need for a dental implant which can be implanted using a simple and reliable implantation procedure. As set out above, the use of shape memory polymers in the field of dental implants has been extremely limited and has not been used in an implant that addresses these needs. It has now been determined that the provision of an implantable dental device which comprises shape memory polymer arranged to directly contact the walls of an implant cavity, allows instant fixation with a simple implantation procedure and enhanced long term fixation to be achieved. The invention therefore provides an implantable dental device which addresses the needs set out above.

Accordingly, in a first aspect the invention provides an implantable dental device comprising:

a root member for implantation into a cavity in alveolar bone or in the root canal space of a tooth, wherein at least a portion of the root member comprises polymeric shape memory material which is activatable from a deformed state to a relaxed state and wherein the root member is provided as an implantable unit comprising both internal and external structure.

In a preferred embodiment of the dental device, the root member comprises a first end, a second end distal thereto and an outer surface which extends between the first end and the second end, wherein at least a portion of the outer surface of the root member is defined by polymeric shape memory material. Preferably, the root member is arranged to provide direct contact of at least a portion of the outer surface of the root member comprising polymeric shape memory material with the wall of an implantation cavity when the device is inserted therein. Preferably, the extent of the outer surface which is defined by polymeric shape memory material directly contacts the wall of the cavity in its relaxed state.

In a second aspect, the invention provides an implantable dental device comprising a root member for implantation into a cavity in alveolar bone or in the root canal space of a tooth, wherein at least a portion of the root member comprises polymeric shape memory material which is activatable from a deformed state to a relaxed state and wherein the root member comprises a first end, a second end distal thereto and an outer surface which extends between the first end and the second end, wherein at least a portion of the outer surface of the root member is defined by polymeric shape memory material.

Preferably, the root member is arranged to provide direct contact of at least a portion of the outer surface comprising polymeric shape memory material with the wall of the implantation cavity when the device is inserted therein. Preferably, the root member is an implantable unit comprising both internal and external structure.

Preferred features and advantages described herein are applicable to a device of the first aspect of the invention and of the second aspect of the invention.

In the deformed state the root member can be inserted in the cavity and in the relaxed state, the root member is arranged to be anchored in the cavity. The root member comprises both an external structure arranged to contact an implantation cavity, preferably directly and provide fixation thereto and an internal structure, arranged to provide support to the root member enabling the implanted device to strengthen bone or tooth in which it is implanted and/or provide support for attachment of a dental prosthesis. The root member is preferably substantially solid.

Preferably, the root member is implantable as a single unit. Advantageously, it is not necessary to introduce any additional component of the root member after implantation in order to achieve activation of the polymeric shape memory material.

Advantageously, an implantable dental device according to the present invention provides instant fixation of the device on activation of the polymeric shape memory material to a relaxed state.

A body of polymeric shape memory material resides macroscopically in one shape when in its deformed state and in another shape when in its relaxed state. Activation from the deformed to the relaxed state is caused by an input of energy. The consequent shape change results in expansion of any portion of the root member comprising polymeric shape memory material and this acts to anchor the device in the implantation cavity. Preferably, the root member is of generally elongate shape, having a longitudinal axis extending from a first end to a second end. Preferably, the shape change on relaxation from a deformed state to a relaxed state results in lateral expansion of any portion of the root member comprising shape memory polymer. When the root member is generally cylindrical, conical or the like, the lateral expansion is radial expansion.

Advantageously, expansion caused by relaxation of the shape memory polymer is effective to cause a portion of the root member to expand laterally to meet the walls of the cavity. The root member is sized such that expansion occurs until further expansion is prevented by contact with the cavity walls. This provides a tight fit of the implanted device within the cavity and consequently good instant fixation, reducing chances of implant failure. Stable instant fixation allows time for surrounding tissues to integrate with the device, for example allowing osseointegration to occur. The provision of instant fixation by relaxation of the shape memory material can advantageously avoid the need for use of cements to provide instant fixation to the device prior and reduces the risk of implant failure prior to long-term fixation.

Furthermore, the use of a polymeric shape memory material provides a degree of flexibility with regard to the size of cavity an implant can be fixated within.

Relaxation of polymeric shape memory material causes a compressive force to be exerted on walls of the cavity in which the root member is inserted. As well as providing a tight fit, it has been shown that the application of compressive forces on tissue can stimulate biological processes, for example osseointegration. Thus, lateral expansion of the shape memory material causes compressive force to be exerted on walls of the implantation cavity, acting to stimulate osseointegration with alveolar bone, increasing the speed with which long-term implant integration is achieved.

The outer surface of the root member of a device of the invention may be smooth, but more preferably defines ridges and/or recesses. Preferably, the outer surface defines a screw thread.

Advantageously, a device of the invention does not require the use of any sleeve or outer covering, but is arranged to provide direct contact of the outer surface with the wall of the implantation cavity and can therefore be inserted directly therein.

In a preferred embodiment, the device further comprises an abutment for receiving a dental prosthesis or crown, wherein the abutment extends from adjacent the first end of the root member.

The device of the invention is preferably implantable as a single unit, i.e. as a unitary device, in which the abutment is connected to the root member, preferably directly. The device may be manufactured from a number of component parts which, prior to implantation are assembled securely together to form a single unit. Alternatively, the root member and the abutment are provided as separate components that can be assembled prior to or after implantation of the root member within an implantation cavity.

In a preferred embodiment, the root member comprises two or more portions, wherein at least one portion comprises polymeric shape memory material.

The polymeric shape memory material may be any biocompatible polymeric shape memory material and may be resorbable and/or non-resorbable. When the device is intended for implantation into alveolar bone, the polymeric shape memory material is preferably resorbable and when the device is intended for implantation into a root canal space of a tooth, the polymeric shape memory material is preferably non-resorbable.

If resorbable polymeric shape memory material is used, over time as osseointegration occurs the material will be resorbed and replaced by newly formed bone. The use of resorbable shape memory material imparts the device with osteoconductive properties, allowing, over time, the implantation cavity to be populated with regenerated bone cells. This is desirable for long-term-integration of the device.

A further advantage achieved when polymeric materials are used in an implantable dental device relates to stiffness of the device. By forming the device in part or in full from polymeric materials, it is possible to achieve a stiffness that resembles the stiffness of alveolar bone or dental tissue. This decreases the risk of stress shielding, an undesirable result that can be observed when implant materials are stiffer than the bone or dental tissue in which they are implanted.

Yet a further advantage of an implantable dental device of the invention is the ability to address the problem of poor fixation in poor quality bone or dental tissue by allowing adaptation of the shape of the implantation cavity. A dental device of the invention can be implanted into a cavity having varying diameter and lateral expansion of polymeric shape memory material into such a cavity improves fixation. Generally, in an area of poor quality bone or dental tissue, the quality improves deeper within the tissue. Thus, a cavity can be drilled to have a small diameter adjacent the mouth of the cavity, with a greater diameter distal thereto. A device according to the invention can expand to fixate within such a cavity, providing increased fixation distal to the mouth of the cavity, where tissue quality is likely to be best.

In a preferred embodiment, the root member comprises at least one portion comprising non-shape memory material and at least one portion comprising polymeric shape memory material. The non-shape memory material is preferably non-resorbable and may comprise titanium, a titanium alloy, stainless steel, a ceramics material or a polymeric material.

In a preferred embodiment, the root member comprises at least one portion comprising non-resorbable material. The non-resorbable material may comprise shape memory material or non-shape memory material.

Thus, in a preferred embodiment, the root member comprises at least one portion comprising polymeric shape memory material, and at least one portion comprising a non-shape memory material. A combination of shape memory material and non-shape memory material advantageously allows control of the relaxation profile of the shape memory material. The geometry of the non-shape memory portion or portions of the root member acts to control the relaxation profile of the shape memory portions of the device. By designing the non-shape memory portions, for instance by providing an indentation in a body of non-shape memory material in which shape memory material can be housed, it is possible to control the relaxation profile of the polymeric shape memory material. The non-shape memory material is arranged to abut the polymeric shape memory material such that on relaxation it is allowed to expand laterally, but not longitudinally.

Thus, in a preferred embodiment, the root member comprises at least one portion comprising polymeric shape memory material and at least one portion comprising non-shape memory material, wherein the portion comprising non-shape memory material is arranged to abut the portion comprising polymeric shape memory material and abutment of the polymeric shape memory material with the non-shape memory material prevents longitudinal expansion of the polymeric shape memory material on relaxation and allows lateral expansion and thereof.

Preferably, the root member comprises a collar portion comprising polymeric shape memory material. The collar portion is preferably arranged to encircle the entire circumference of the root member along at least a portion of its length. On relaxation and lateral expansion of the collar it contacts the entire circumference of an implantation cavity in which the device is implanted thereby forming a seal between the device and the implantation cavity.

Preferably, the collar portion is arranged to prevent longitudinal expansion of the polymeric shape memory material, for example, the collar portion is arranged to abut non-shape memory material of the abutment or one or more non-shape memory material portions of the root member such that on relaxation, the polymeric shape memory material is allowed to expand laterally, but longitudinal expansion is constrained.

In use, the second end of the root member inserted first into an implantation cavity, such that the first end lies proximal to the mouth of the cavity. Depending on the intended use of the device, the first end may lie above, below or level with the mouth of the cavity. Preferably, the collar is positioned at the first end of the root member.

A collar portion positioned at the first end of the root member provides, on relaxation of the polymeric shape memory material, a seal between the device and the implantation cavity at or near the mouth of the cavity. Arrangement of the collar portion whereby lateral expansion of the polymeric shape memory material is constrained prevents the collar portion extending above the mouth of the cavity on relaxation. Advantageously, this seal acts as a barrier to prevent entry into the cavity of bacteria thereby reducing risk of infection which can lead to implant failure. In addition, the seal acts as a barrier to prevent in-growth of soft tissue into the implant cavity. Soft tissue in-growth into an implant cavity and fibrous tissue formation which can be caused thereby, can be contributory factors leading to implant failure.

Preferably, the collar portion comprises resorbable polymeric shape memory material. Use of resorbable polymer is particularly preferably when the device is for implantation into alveolar bone. Use of resorbable material in the collar portion may act to encourage surface soft tissue growth whilst preventing entry of soft tissue into the implant cavity. This combats a problem observed with known implant devices, in which gum fails to regenerate right up to a prosthesis attached to an abutment. This can leave a gap between gum and a prosthesis which is not an aesthetically pleasing result. The provision of a resorbable collar may have a tissue conductive effect, encouraging the growth of surface soft tissue right up to the abutment as the collar resorbs.

In a preferred embodiment, the root member comprises a body comprising non-resorbable material, wherein the body defines one or more indentations which house one or more portions of polymeric shape memory material. Preferably, the one or more indentations are in the form of elongate recesses which house one or more elongate portions comprising polymeric shape memory material. Preferably, the root member comprises a plurality of elongate portions arranged to extend longitudinally along some or all of the length of the root member from the first end to the second end. Alternatively, the root member comprises an elongate portion arranged in a helical, coiled or mesh formation around the body. Preferably, the body comprises an indentation which extends around the outer surface of the root member adjacent the first end, such that polymeric shape memory material located within the indentation forms the collar portion of the root member. Preferably, the body comprises non-shape memory material.

In an alternative embodiment, the root member comprises a body comprising resorbable polymeric shape memory material, wherein the body defines one or more indentations which house one more portions of non-resorbable material, non-shape memory material.

In a preferred embodiment, the root member comprises two or more adjoining segments, wherein at least one segment comprises polymeric shape memory material and at least one segment comprises non-resorbable material. Any segment comprising polymeric shape memory material may, independently, comprise an internal portion comprising non-resorbable material, encapsulated by the polymeric shape memory material. Preferably, the internal portion extends substantially along the central longitudinal axis of the root member and does not contact the outer surface of the root member or contact the outer surface of the root member only at the second end. The non-resorbable material may be shape memory material or non-shape memory material, preferably non-shape memory material. The polymeric shape memory material may be resorbable or non-resorbable.

Preferably, a segment at the first end of the root member, adjacent the abutment, comprises polymeric shape memory material, thus providing a collar of the root member. The collar is located, on implantation of the device into an implantation cavity, proximal to the mouth of the implantation cavity.

In a preferred embodiment, the root member comprises a plurality of adjoined segments, a first population of segments comprising resorbable shape memory material and a second population of segments comprising non-resorbable material. Preferably, the plurality of segments are arranged in an alternating sequence along some or all of the length of the root member, alternating between members of the first population and the second population. The non-resorbable material may be shape memory material or non-shape memory material. In an alternative arrangement, the first population of segments comprises non-resorbable polymeric shape memory material and the second population of segments comprises non-shape memory material.

In a preferred embodiment, the root member comprises an internal portion comprising non-resorbable material. The non-resorbable material may be shape memory material or non-shape memory material. Preferably, the internal portion either does not contact the outer surface of the root member, or contacts the outer surface of the root member only at the second end. Preferably, the non-resorbable internal portion is encapsulated by an outer portion of polymeric shape memory material. Preferably, the internal portion extends substantially along the longitudinal axis of the root member. The internal portion can extend along a portion of the length or all of the length of the root member from the first end to the second end.

In an alternative embodiment, the root member comprises an outer portion comprising non-resorbable material, and an inner portion comprising polymeric shape memory material, wherein the outer portion is arranged to partially encapsulate the inner portion. The outer portion defines at least one opening though which polymeric shape memory material of the inner portion can extend on relaxation. The non-resorbable material may be shape memory material and/or non-shape memory material.

In a preferred embodiment, one or more active agent is incorporated into the dental device. Suitable active agents include bone morphogenic proteins, antibiotics, anti-inflammatories, angiogenic factors, osteogenic factors, monobutyrin, omental extracts, thrombin, modified proteins, platelet rich plasma/solution, platelet poor plasma/solution, bone marrow aspirate, and any cells sourced from flora or fauna, such as living cells, preserved cells, dormant cells, and dead cells. It will be appreciated that other bioactive agents known to one of ordinary skill in the art may also be used. Preferably, the active agent is incorporated into the polymeric shape memory material, to be released during the relaxation or degradation of the polymer material. Advantageously, the incorporation of an active agent can act to combat infection at the site of implantation and/or to promote new tissue growth.

Preferably, the dental device is of a generally elongate shape, wherein the abutment is located at a first end and the root member extends from adjacent the abutment to a second end. Preferably, the dental device is generally cylindrical or is formed in a screw-shape. However, other shapes are contemplated. A cylindrical device is of particular use as a dental post for insertion into a root canal space and a screw-shaped device is of particular use for insertion into an alveolar bone cavity.

In a preferred embodiment, the root member is formed from a single contiguous portion comprising polymeric shape memory material. Preferably, the single portion is formed solely from polymeric shape memory material or polymeric material incorporating one or more active agents.

In a preferred embodiment, the root member of a dental device comprises reinforced polymeric material. Preferably, the reinforced polymeric material comprises a composite or matrix including reinforcing material or phases such as fibers, rods, platelets, and fillers. More preferably, the polymeric material can include glass fibers, carbon fibers, polymeric fibers, ceramic fibers, or ceramic particulates. Other reinforcing material or phases known to one of ordinary skill in the art could also be used.

In a preferred embodiment, the dental device comprises a combination of metal or metal alloy, preferably titanium or a titanium alloy, and polymeric shape memory material.

In a preferred embodiment, one or more material from which the device is formed is porous. Porosity can allow infiltration by cell from surrounding tissues, enhancing integration of the device by processes such as osseointegration.

In a preferred embodiment, the device is provided with a bone graft, bone graft substitute or cement to aid fixation into poor quality bone or dental tissue.

In a preferred embodiment, the device is provided with a tooth prosthesis, for example a crown, attached to the abutment prior to implantation of the device.

In a preferred embodiment, the implantable dental device of the invention is an implantable dental post for implantation into a root canal space of a tooth.

In a third aspect, the present invention provides a method of implantation of an implantable dental device according to the first aspect of the invention into a cavity within alveolar bone of the jaw, wherein the method comprises the steps of:
 a) drilling a cavity in alveolar bone of the jaw,
 b) inserting the second end of the root member into the cavity, and
 c) activating the polymeric shape memory portion(s) of the root member to cause relaxation thereof, thereby fixating the root member within the cavity.

In a preferred embodiment, prior to step a) a tooth to be replaced by a dental prosthesis attached to the abutment of the implanted dental device is removed.

In a preferred embodiment, the drilled cavity is non-circular, for example oval, in shape. The provision of an oval shape, for example, would make the polymeric shape memory material expand and fixate so that the torque force required to move the implant would be larger than if a circular cavity was used.

In a preferred embodiment, the diameter of the cavity is varied at different depths of the cavity. Expansion of polymeric shape memory material into portions of the cavity having greater diameter will enhance fixation of the device.

In a preferred embodiment, the cavity is cleaned before insertion of the root member.

In a preferred embodiment, insertion of the root member comprises simple insertion or insertion by screwing.

In a preferred embodiment, activation of the polymeric shape memory material is achieved by supplying the polymeric shape memory material with energy that exceeds the glass transition temperature (Tg) of the material. Preferably, exposure of the device to body temperature is sufficient to cause activation. Alternatively, energy is supplied by use of a heat or light source.

In a preferred embodiment, the implantable dental device comprises and abutment and the method additionally comprises step d) of attaching a dental prosthesis, for example a crown, to the abutment.

In a fourth aspect, the present invention provides a method for implantation of an implantable dental device according to the first aspect of the invention into a cavity within a root canal space of a tooth, wherein the method comprises the steps of:
 a) preparing a tooth by drilling a cavity in a root canal,
 b) inserting the second end of the root member into the drilled cavity, and
 c) activating the polymeric shape memory portion(s) of the root member to cause relaxation thereof, thereby fixating the root member within the cavity.

Preferred embodiments set out for the third aspect of the invention are also applicable to the fourth aspect of the invention.

In a preferred embodiment, the method additionally comprises step d) of covering the first end of the root member prior to implantation with a layer of a material suitable to form a hard surface, for example methyl methacrylate.

In a fifth aspect, the invention provides a kit comprising a dental device according to the first or second aspect of the invention and a dental prosthesis for attachment thereto after implantation of the device.

It should be appreciated that combinations of the preferred features set out above are contemplated within the scope of the invention.

Additional features and advantages of the invention will be apparent from the following description of specific embodiments of the invention. Specific embodiments are illustrated, by way of example, in the accompanying drawings.

BRIEF DESCRIPTION OF THE DRAWINGS

FIG. 17A shows the device in the deformed configuration in which it is inserted into a root canal cavity and FIG. 17B shows the device, after activation of the polymeric shape memory material, in its relaxed configuration.

DETAILED DESCRIPTION

Figure 1:
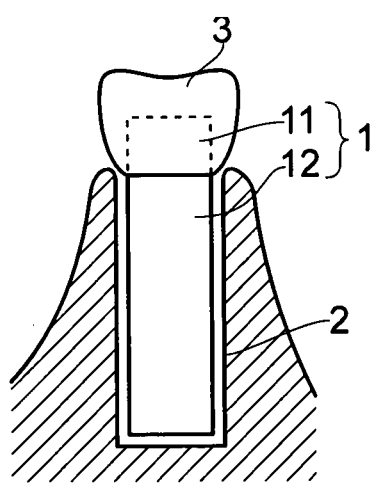
FIG. 1 shows a cross-sectional view of an implantable dental device according to a specific embodiment of the first aspect of the invention positioned within a cavity in alveolar bone.

An implantable dental device of the invention comprises polymeric shape memory material. Shape memory polymers, which can be resorbable or non-resorbable, are known in the art and any biocompatibly polymeric shape memory material can be used in the context of the present invention. Specific polymers that may be used include polyetheretherketone (PEEK), polymethyl methacrylate (PMMA), polyethyl methacrylate (PEMA), polyacrylate, poly-alpha-hydroxy acids, polycapropactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof.

In a preferred embodiment, the polymeric shape memory material resides in a deformed state below a certain temperature, known as the glass transition temperature (Tg) and is activatable from the deformed state to the relaxed state above this temperature. Generally, polymeric materials that display shape memory properties show a large change in modulus of elasticity at the glass transition temperature ($T_g$). Shape-memory properties are utilized by taking advantage of this characteristic. Namely, a macroscopic body of polymeric shape memory material to which a definite shape (the original shape) has been imparted by molding, can be softened by providing the article with energy and heating to a temperature ($T_f$) higher than the $T_g$ of the polymeric material, but lower than the melting temperature ($T_m$). At this temperature ($T_f$), the material can be deformed into a different macroscopic shape (the deformed state). In the deformed state an oriented polymer network is formed. The polymeric material is then cooled to a temperature lower than the $T_g$, whilst maintaining its deformed state. When the polymeric material is heated again to a temperature higher than the secondary molding temperature $T_f$, but lower than the $T_m$, the deformed state disappears and the polymeric material relaxes to recovered its original shape. The input of energy necessary to cause the polymeric material to relax from its deformation state to its relaxed state in known as activation.

The glass transition temperature of the polymer material will vary based on a variety of factors, such as molecular weight, composition, structure of the polymer, and other factors known to one of ordinary skill in the art and may be in the region of between 35-60° C.

In the context of the present invention, deformation of the polymeric shape memory material is generally achieved prior to implantation of the dental device, generally during manufacture. The input of heat sufficient to reach $T_f$ is achieved using electrical and/or thermal energy sources and this is followed by deformation of the polymeric material. Deformation leads to an oriented polymer network and can be achieved by processes including zone drawing, hydrostatic extrusion, die drawing, compression flow molding, thermoforming, rolling and roll drawing.

The present invention contemplates the use of electrical and thermal energy sources to heat the polymeric material. However, the polymer material could be relaxed via other methods known to those of ordinary skill in the art, including, but not limited to the use of force, or mechanical energy, and/or a solvent. Any suitable force that can be applied either preoperatively or intra-operatively can be used. One example includes the use of ultra sonic devices, which can relax the polymer material with minimal heat generation. The presence of a solvent has a lowering effect on the Tg of a polymeric shape memory material. Solvents can therefore be used to induce relaxation and/or increase the rate of relaxation. Solvents that can be used include organic-based solvents and aqueous-based solvents, including body fluids. Care should be taken that the selected solvent is not contra indicated for the patient, particularly when the solvent is used intra-operatively. The choice of solvents will also be selected based upon the material to be relaxed. Examples of solvents that can be used to relax the polymer material include alcohols, glycols, glycol ethers, oils, fatty acids, acetates, acetylenes, ketones, aromatic hydrocarbon solvents, and chlorinated solvents.

An implantable dental device of the invention for insertion into an implantation cavity within alveolar bone of the jaw or a cavity within the root canal space of a tooth comprises a root member and optionally an abutment which provides means for attachment of a dental prosthesis, for example a crown. The root member is arranged to reside in two configurations, a first configuration (the deformed state) in which it can be inserted into an implantation cavity and a second configuration (the relaxed state) in which the root member is arranged to be anchored in the cavity. At least a portion of the root member comprises polymeric shape memory material. When provided with a required level of energy, the polymeric shape memory material is activatable from the deformed state to the relaxed state. The energy required to activate the shape memory material can be provided in the form of heat, light or a combination thereof. The polymeric shape memory material used in the root member may be formulated such that exposure of the root member to body temperature, on insertion into an alveolar cavity, is sufficient to cause activation.

In use, the polymeric shape memory material present in the root member of the device resides in its deformed state prior to implantation into an implantation cavity. Deformation from the original shape of the shape memory polymer to its deformed state generally involves stretching of the polymer, for example along the longitudinal axis of the root member. Activation of the polymeric shape memory material occurs after the root member has been implanted into the cavity. Relaxation of the polymer on activation and return to the original shape involves expansion of any portion of the root member which comprises polymeric shape memory material. Expansion occurs laterally due to the direction in which the polymeric material is deformed and/or due to abutment of the polymeric material within the root member with non-shape memory portions, with this abutment preventing any expansion other than lateral expansion. Expansion of polymeric shape memory material leads to the root member having a tight fit within the cavity, with the root member directly contacting walls of the cavity and exerting force thereon.

Push-out tests performed on die drawn PLC rods constrained within drilled holes in sawbone demonstrate the improvement to fixation cause by relaxation of an implant comprising polymeric shape memory material. In these tests a PLC rod was inserted into a drilled hole in sawbone and activated to relax by immersion in water at 37° C. for 9 days. The force required to push out a rod increased from 1700N to 1900N.

FIG. 1 shows an implantable dental device 1 positioned within an implantation cavity 2 in alveolar bone. The device 1 comprises an abutment 11 and a root member 12. The root member 12 is inserted into a cavity in alveolar bone when the polymeric shape memory material is in a deformed state. The polymeric shape member material is activated by exposure to body temperature or an external input of energy, for example application of heat or light. Upon activation the polymeric shape member material will relax, causing radial expansion of the root member 12 and fixation thereof in the cavity 2. Once fixated in the cavity a crown 3 can be attached to the abutment 11.

Figure 2:
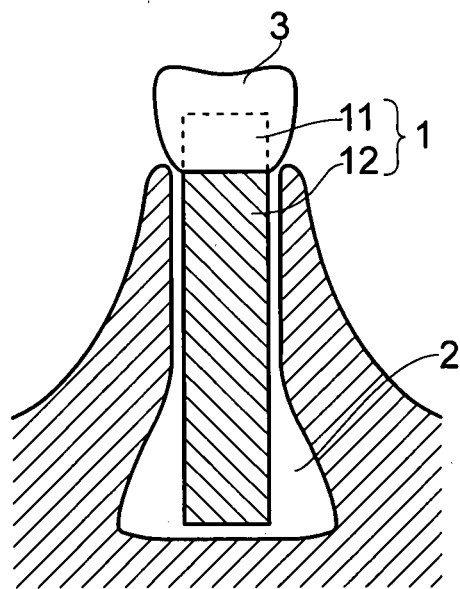
FIGS. 2A and 2B show cross-sectional views of the device positioned within a cavity in alveolar bone in the deformed state (2A) and the relaxed state (2B).
Figure 2:
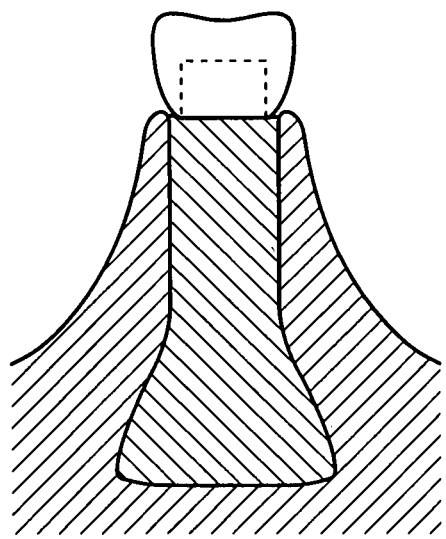

A dental device 1, positioned within an implantation cavity 2 is illustrated in FIGS. 2A and 2B. The cavity 2 has a greater diameter distal to the mouth of the cavity 2 and tapers to a smaller diameter proximal to the mouth of the cavity. The device 1 is shown in its deformed state in FIG. 2A and in its relaxed state in FIG. 2B. As illustrated, on relaxation, lateral expansion of the root member 12 has occurred, causing the root member to contact the walls of the cavity 2 to provide fixation therewith. The taper of the cavity 2 is arranged to provide increased fixation in the area where tissue quality is likely to be best.

Figure 3:
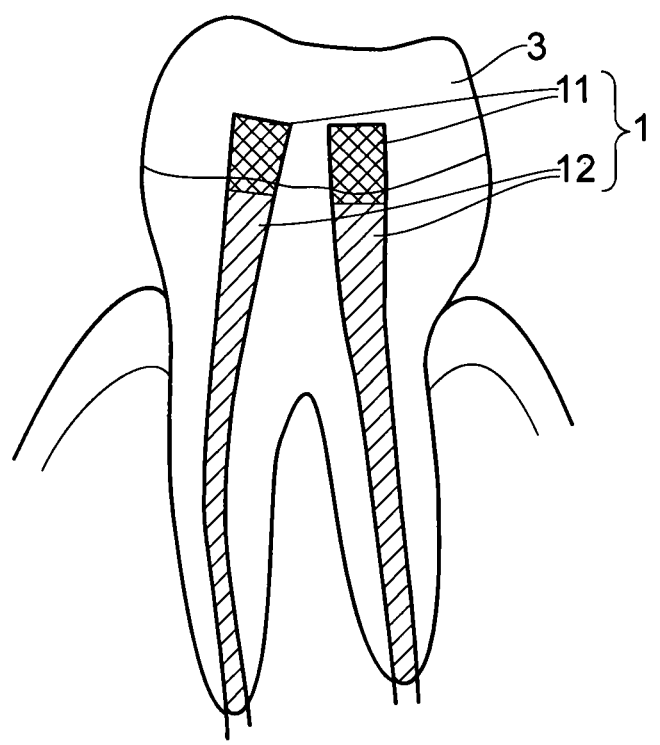
FIG. 3 shows a cross-sectional view of two implantable dental devices according to the invention, implanted within root canal spaces within a tooth and providing means for attachment of a crown.

Another application of an implantable dental device of the invention is shown in FIG. 3, in which two dental devices 1 have been implanted into two cavities within the root canal space of a tooth.

Figure 4:
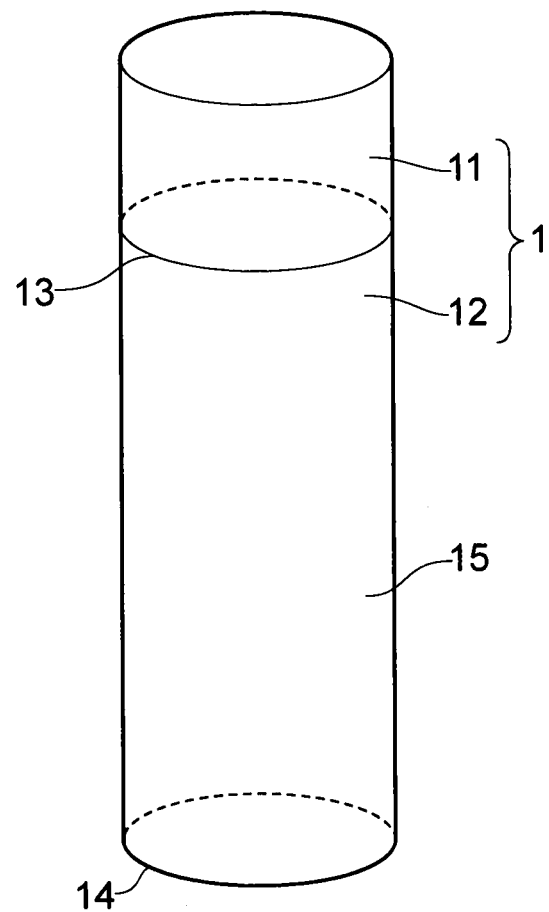
FIGS. 4 to 16 show perspective views of specific embodiments of an implantable dental device of the invention comprising a root member and an abutment.

In one specific embodiment of the invention, as illustrated in FIG. 4, the dental device 1 comprises an abutment 11 and a root member 12. The root member 12 comprises polymeric shape memory material which can be resorbable or non-resorbable. The root member 12 comprises a first end 13 and a second end 14, wherein the first end 13 is adjacent the abutment 11 and the second end 14 is distal thereto. An outer surface 15 of the root member 12 extends between the first end 13 and the second end 14.

Figure 5:
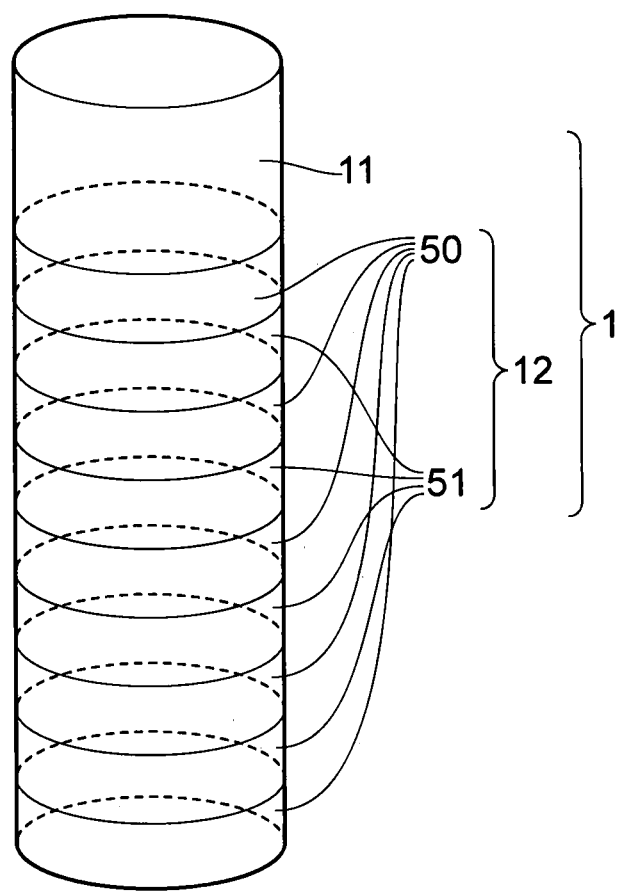

FIG. 5 illustrates a dental fixation device 1 which comprises an abutment 11 and a root member 12. The root member comprises a plurality of adjoined disk-shaped segments with a first population of segments 50 comprising non-resorbable material and a second population of segments 51 comprising polymeric shape memory material. The first and second populations of segments, which may be glued together, form a stack and are arranged in an alternating pattern. A device having the configuration show in FIG. 5 may comprise a first population of segments comprising non-resorbable shape memory material and a second population of segments comprising non-shape memory material. Alternatively, a device having the configuration set out in FIG. 5 may comprise a first population of segments comprising non-resorbable non-shape memory or shape memory material and a second population of segments comprising resorbable polymeric shape memory material.

Figure 6:
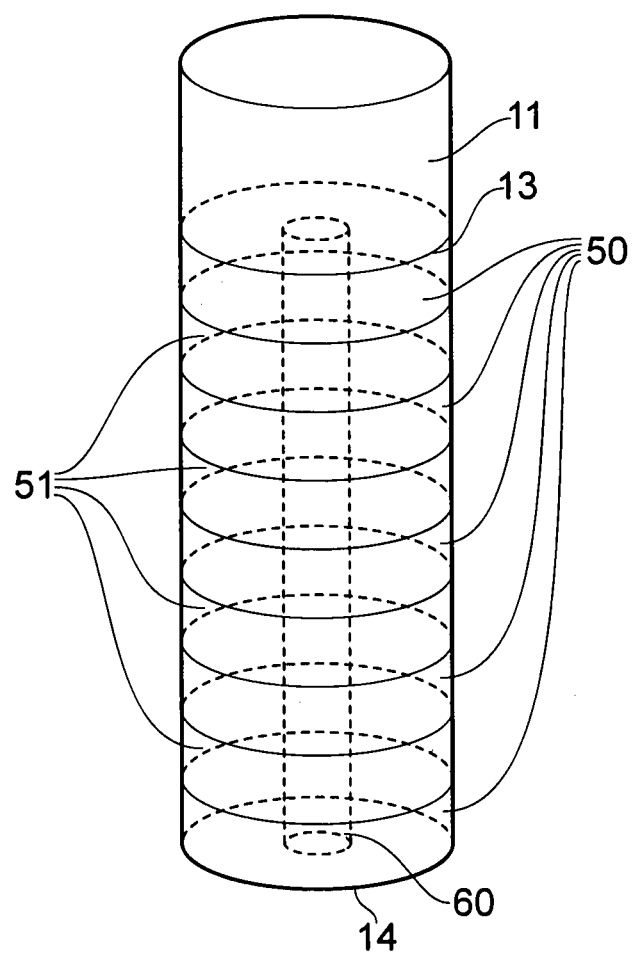

FIG. 6 illustrates a device as shown in FIG. 5, additionally comprising a rod-like internal portion 60 comprising non-resorbable material. The internal portion 60 is encapsulated by the first and second populations of segments and contacts the outer surface of the root member only at the second end 14.

Figure 7:
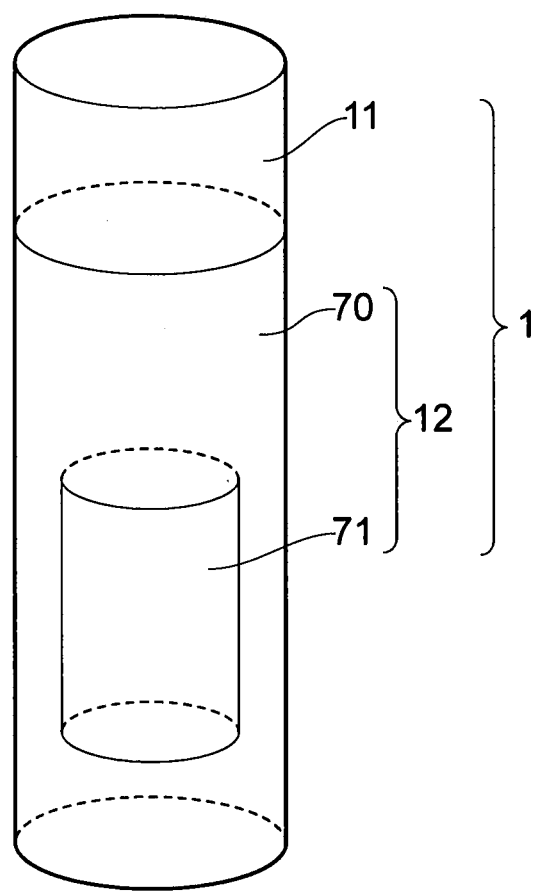

An alternative embodiment of a dental device 1 is illustrated in FIG. 7, in which the root member 12 comprises an outer portion 70 comprising non-resorbable material and an inner portion 71 comprising polymeric shape memory material. The outer portion 70 is arranged to partially encapsulate the inner portion 71. The outer portion 70 has a substantially solid structure defining a void in which the inner portion 71 is located. The outer portion defines at least one opening contiguous with the void, such that the polymeric shape memory material of the inner portion can extend therethrough on relaxation. Once inserted into a cavity, and upon activation, the polymeric shape-memory material of the inner portion 71 will relax and expand through the opening to anchor against the walls of the implantation cavity. The inner portion may comprises resorbable or non-resorbable polymeric shape memory material. A device of this embodiment may be supplied to a dental practitioner with the void filled with polymeric shape memory material or as a kit comprising the device with the void unfilled, for the practitioner to fill themselves prior to implantation of the device.

Figure 8:
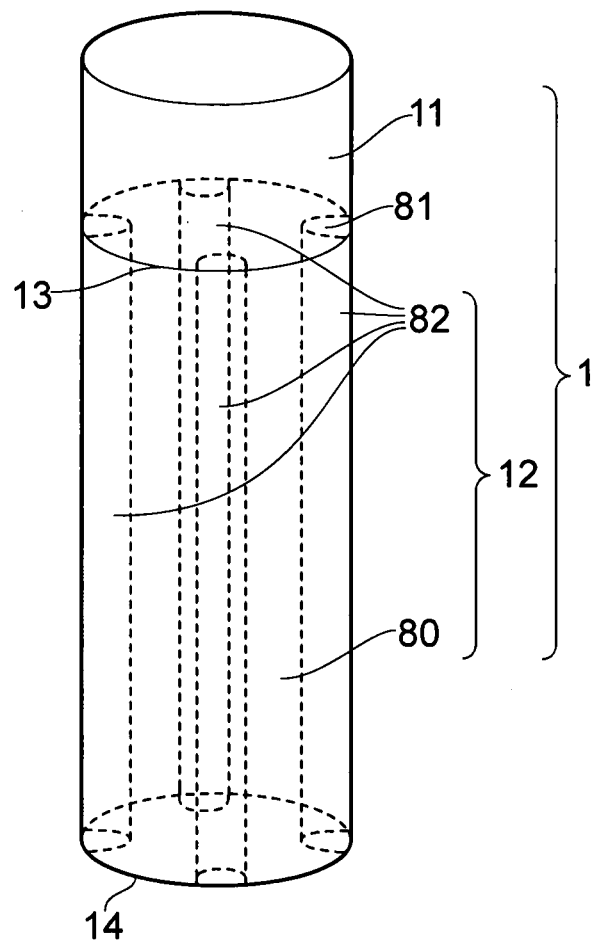
Figure 9:
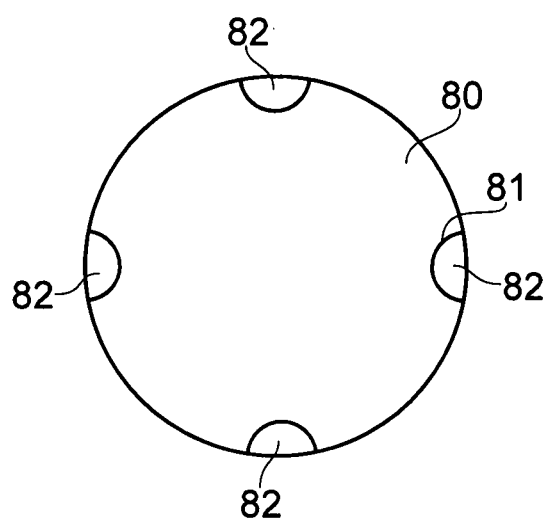

FIGS. 8 and 9 illustrate a dental device 1 wherein the root member 12 comprises a body 80 comprising non-resorbable material. The body 80 is provided with longitudinal indentations 81 in which elongate portions 82 of polymeric shape memory material are positioned. The elongate portions 82 are positioned so as to define a portion of the outer surface of the root member 12 and extend longitudinally between the first end 13 and the second end 14 of the root member. In the illustrated embodiment four elongate portions spaced equally about the outer surface of the root member 12 are shown. Any number of elongate portions 82 could be present. The elongate portions 82 may comprise resorbable polymeric material. Location of the elongate portions 82 within indentations 81 means that, upon relaxation of the polymeric shape memory material of the elongate portions 82, only radial/lateral expansion of the polymeric material is permitted. Expansion in any other direction is constrained by abutment of the elongate portions 82 with walls of the indentations 81. The elongate portions 82 may be secured within the indentations 81 with glue or by mechanical attachment.

In an alternative configuration of the embodiment shown in FIG. 9, the body 80 comprises resorbable polymeric shape memory material and defines one or more indentations 81 which house one or more elongate portions 82 of non-resorbable material.

Figure 10:
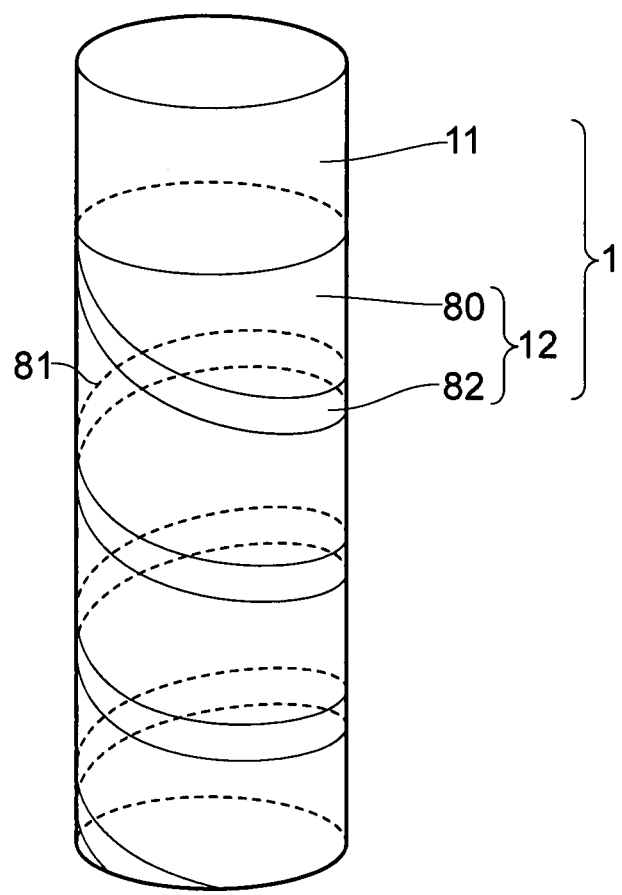

FIG. 10 illustrates an embodiment of a dental device 1 wherein the root member 12 comprises a body 80 comprising non-resorbable material defining an indentation 81 which houses an elongate portion 82 comprising polymeric shape memory material. The indentation 81 and elongate portion 82 are arranged in a coil formation around the body 80.

Figure 11:
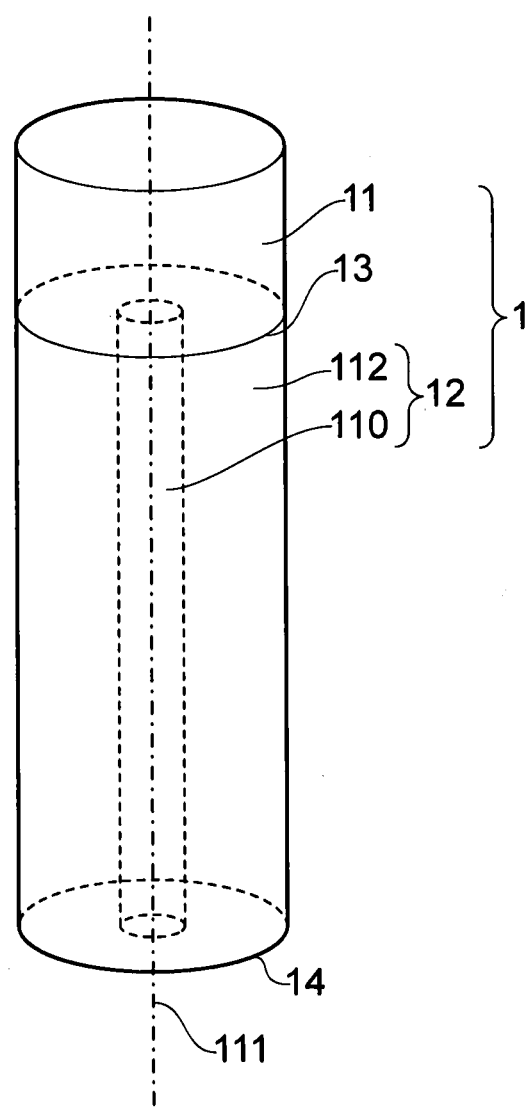

The dental device 1 illustrated in FIG. 11 comprises a root member comprising an internal portion 110 in the form of a rod extending from adjacent the first end 13 of the root member 12 along the longitudinal access 111 of the root member 12 to the second end 14. The internal portion 110 comprises non-resorbable material and is encapsulated by an outer portion 112 comprising polymeric shape memory material. The outer portion 112 may comprise resorbable or non-resorbable polymeric shape memory material. The internal portion acts as a structural reinforcement for the root member and is attachable within the outer portion 112 by gluing or mechanical attachment, for example a screw attachment.

FIGS. 12 to 17 illustrate various configurations of dental device 1 wherein the root member 12 comprises adjoined segments.

Figure 12:
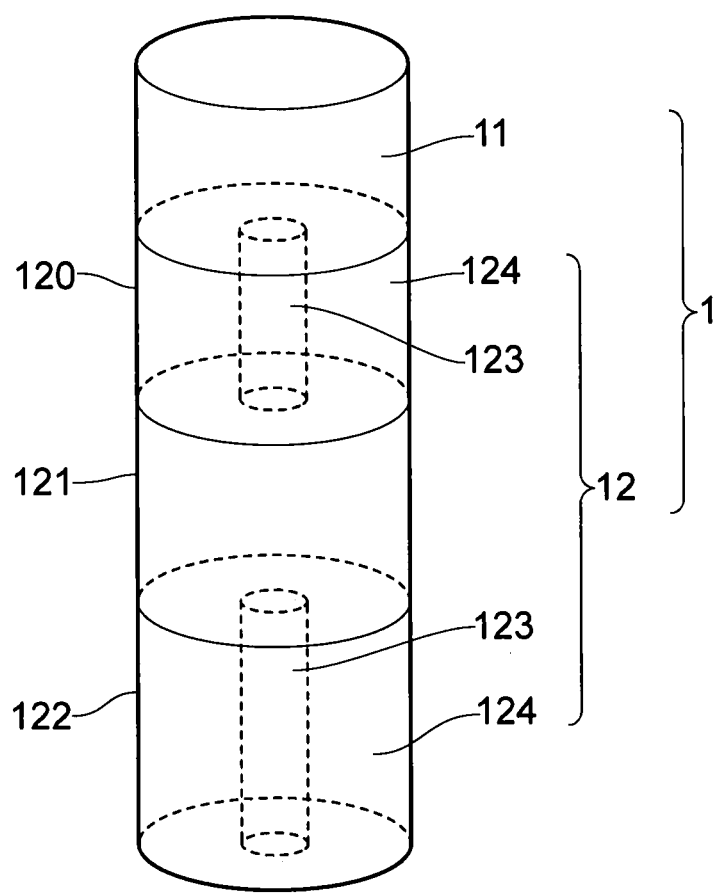

In the device shown in FIG. 12, the root member 12 comprises a first segment 120, a second segment 121 and a third segment 122. The first and third segments 120, 122 comprise a rod-like internal portion 123 comprising non-resorbable material encapsulated by an outer portion 124 comprising polymeric shape memory material. The second segment 121 comprises non-resorbable material. The first segment 120 is positioned at the first end 13 of the root member 12, adjacent the abutment 11, the third segment 122 is positioned at the second end 14 of the root member 12 and the second segment 121 is positioned between the third and first segments. In one configuration of this device the outer portions 124 comprises resorbable polymeric shape memory material and the internal portions 123 and the second segment 121, independently, comprise non-resorbable non-shape memory or shape memory material. In an alternative configuration, the outer portions 124 comprise non-resorbable polymeric shape memory material and the inner portions and the second segment 121, independently, comprise non-resorbable non-shape memory material.

The adjoined segments may be joined together by gluing or they may be attached mechanically, for example by being screwed together.

Figure 13:
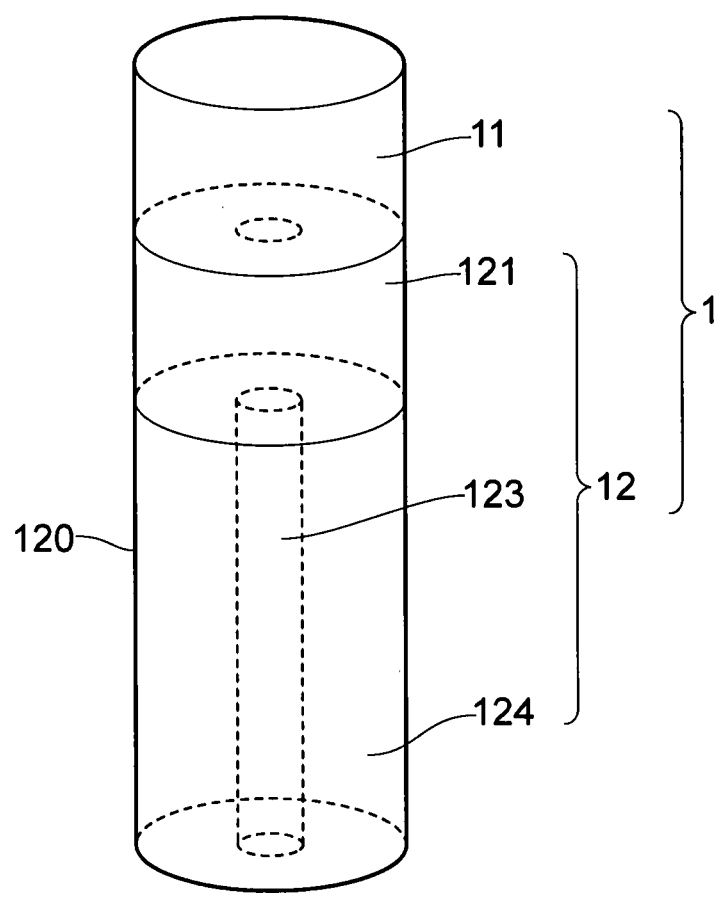

An alternative arrangement of a segmented root member is illustrated in FIG. 13, in which the root member 12 comprises a first segment 120 and a second segment 121 as defined above. The second segment 121 is positioned at the first end 13 of the root member 12, adjacent the abutment 11 and the first segment 120 is positioned adjacent the second segment 121, at the second end 14 of the root member 12.

Figure 14:
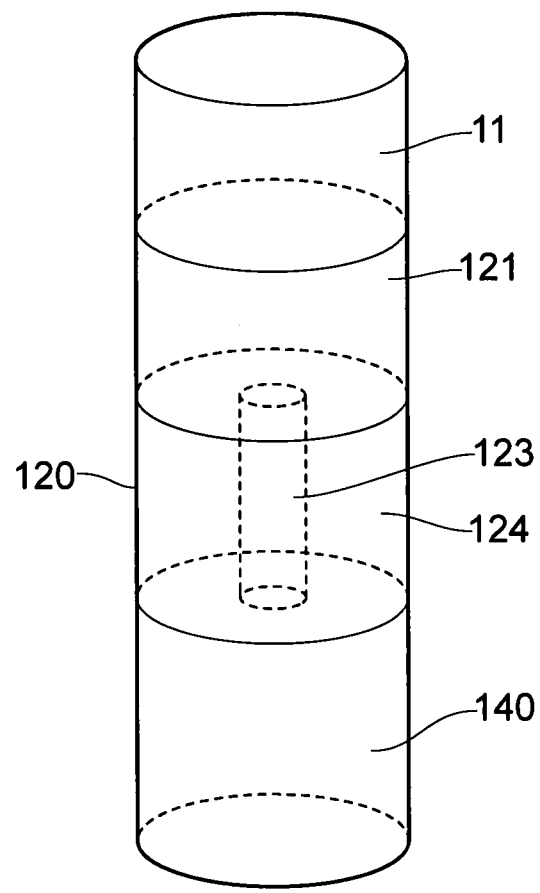

A further alternative arrangement of a segmented device is illustrated in FIG. 14. In this arrangement the root member 12 comprises first, second and third segments, wherein the first and second segments 120, 121 are as defined above in respect of FIGS. 12 and 13 and the third segment 140 comprises non-resorbable material. The second segment 122 is positioned adjacent the abutment 11, the third segment 140 is positioned adjacent the second end 14 of the root member 12 and the first segment 120 is position between the second segment 121 and the third segment 140. In this arrangement, the second and third segments may comprise non-resorbable, non-shape memory material which abuts the outer portion 124 comprising polymeric shape memory material, so as to allow only lateral expansion thereof.

Figure 15:
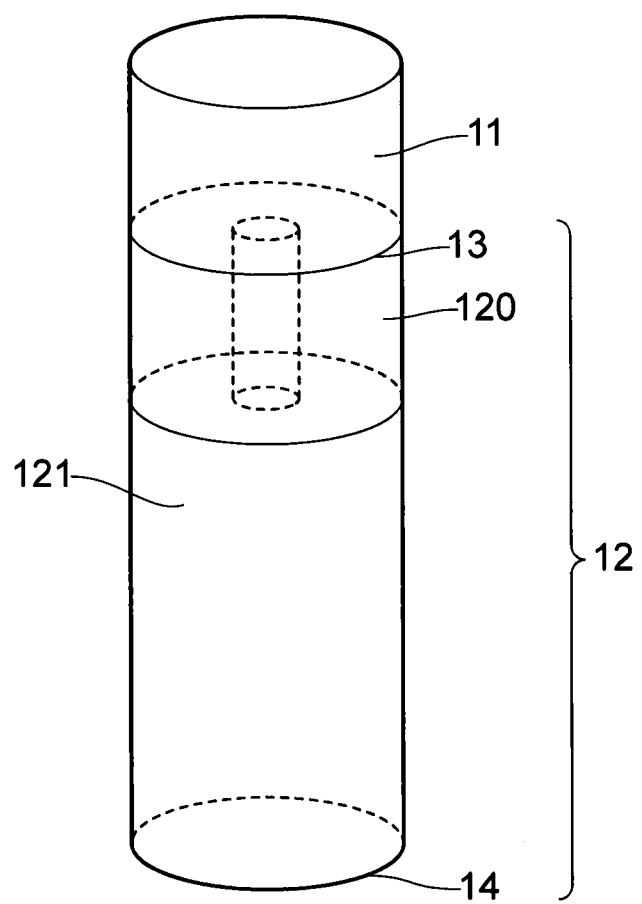

Yet a further arrangement of a segmented fixation device is shown in FIG. 15, in which the root member 12 comprising a first segment 120 as defined above, located at the first end 13 of the root member 12 and a second segment 121, as defined above, located adjacent thereto.

Figure 16:
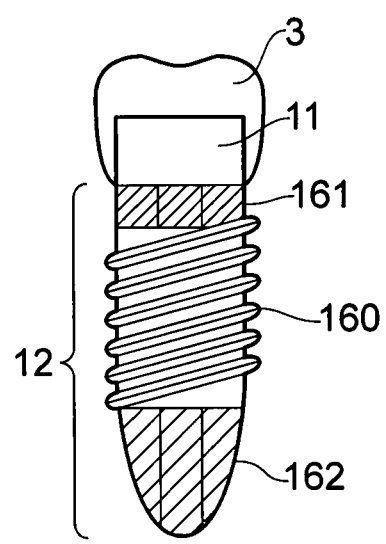

An implantable dental device 1 configured for implantation into an alveolar bone cavity is illustrated in FIG. 16. The device 1 comprises an abutment 11 and a root member 12. The root member 12 is formed from a body 160 in the form of a titanium, titanium alloy or stainless steel screw. The root member 12 comprises an upper collar 161 and a lower collar 162 located on either side of the body 160, both of which comprise polymeric shape memory material. In use, the upper collar 161, being located at the first end of the root member 12 will expand to form a seal between the device and the mouth of an implantation cavity. The lower collar 162, on relaxation, acts to provide instant fixation of the device at the base of the cavity.

Figure 17A:
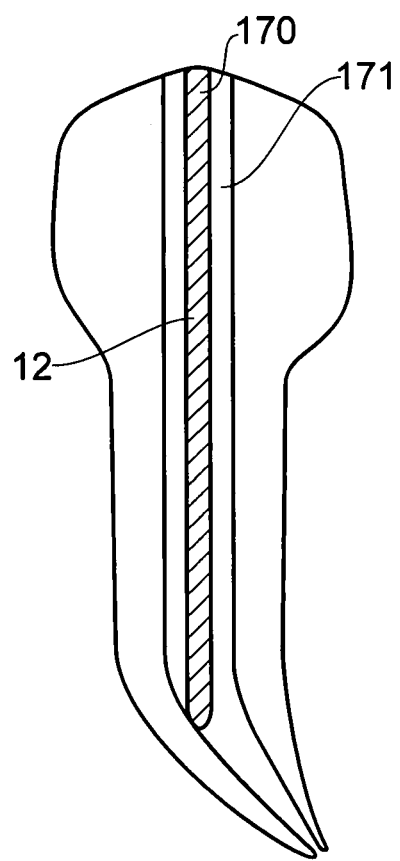
FIGS. 17A and 17B show cross-sectional views of an implantable dental device comprising a root member, fixated within a root canal space of a tooth.
Figure 17B:
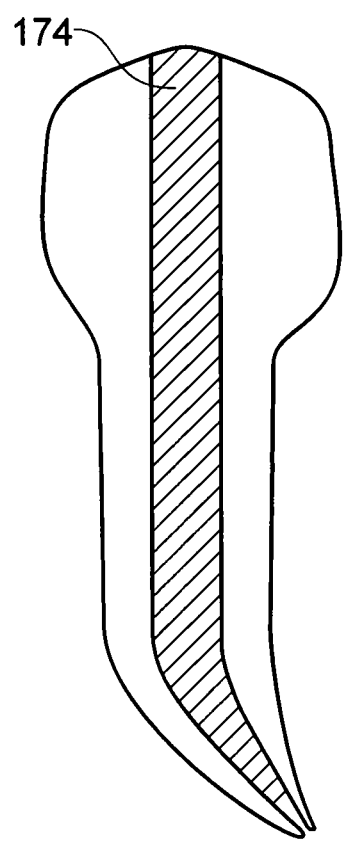

The present invention additionally provides an implantable dental device consisting solely of a root member, which is particularly suitable for use as a dental post for insertion into a cavity within the root canal space of a tooth to provide reinforcement to the existing structure of the tooth. A device 170 according to this embodiment of the invention is illustrated in use in FIGS. 17A and 17B. FIG. 17A shows the device 170 in the deformed configuration in which it is inserted into a root canal cavity 171 and FIG. 17B shows the device, after activation of the polymeric shape memory material, in its relaxed configuration. In the relaxed configuration, the device 170 is expanded to provide fixation within the cavity 171.

Various specific embodiments of a dental device consisting solely of a root member are illustrated in FIGS. 18 to 24. In all embodiments, at least a portion of the root member comprises polymeric shape memory material.

Figure 18:
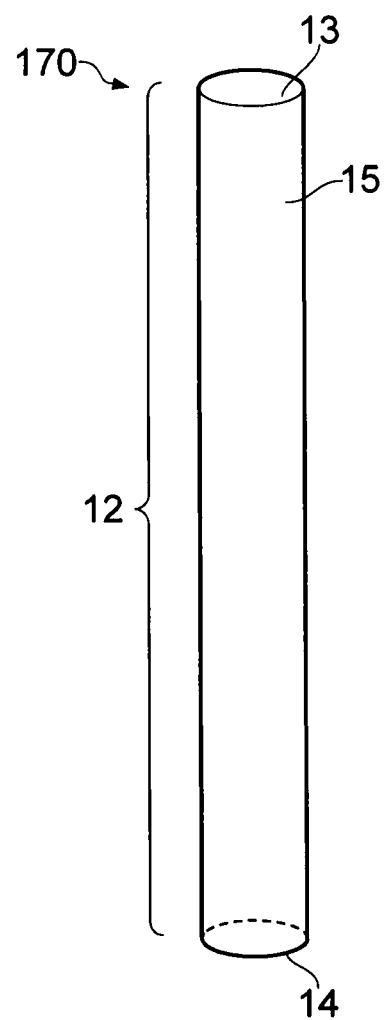
FIGS. 18 to 24 show perspective views of specific embodiments of an implantable dental device of the invention which are suitable for use as a dental post.

FIG. 18 shows a dental post 170 comprising a root member 12 formed from a single contiguous portion formed solely of polymeric shape-memory material. The root member comprises a first end 13, a second end 14 distal thereto and an outer surface 15 which extends between the first end 13 and the second end 14. The post is arranged to provide direct contact of at least a portion, and preferably all, of the outer surface 15 with the wall of the implantation cavity in which it is inserted when the polymeric shape memory material is in its relaxed state (shown in FIG. 17B). The polymeric shape memory material is preferably non-resorbable.

Figure 19:
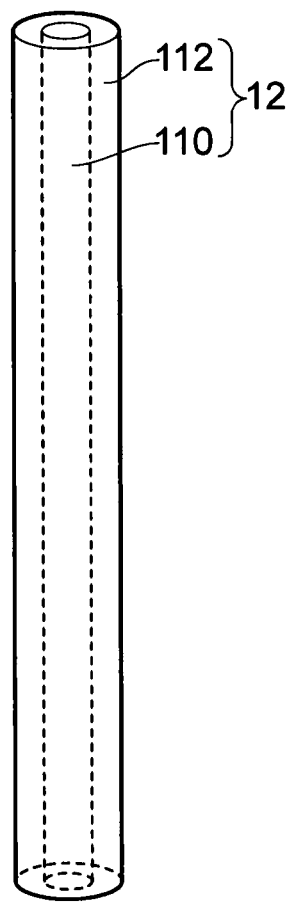

FIG. 19 illustrates a device 170 wherein the root member 12 additionally comprises an internal portion 110 which is formed from non-resorbable, non-shape memory material and which is substantially encapsulated by an outer portion 120 formed of polymeric shape-memory material. The internal portion 110 acts as a structural reinforcement for the root member and is attachable within the outer portion 112 by gluing or mechanical attachment, for example a screw attachment.

Figure 20:
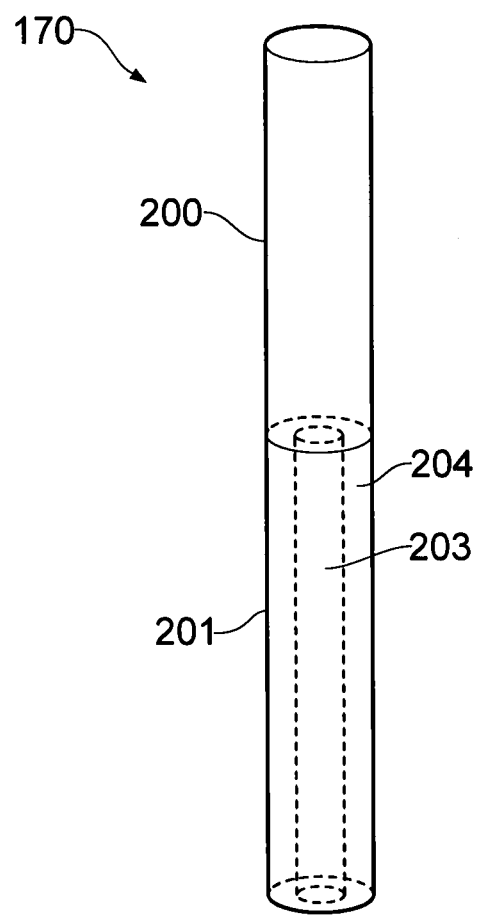
Figure 21:
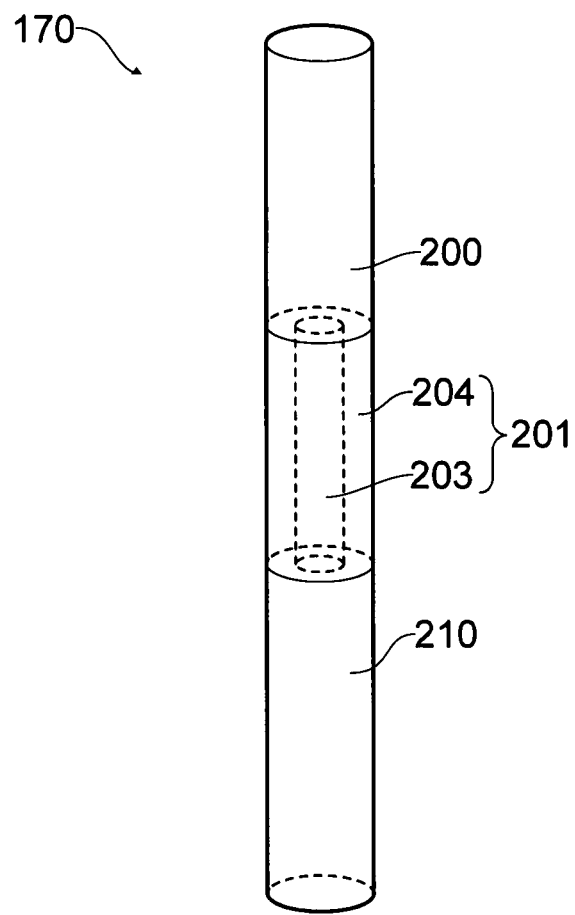

The device may comprise adjoined segments, as illustrated in FIGS. 20 and 21. The device illustrated in FIG. 20 comprises a first segment 200, adjacent the first end 13 of the root member 12 and a second segment 201. The first segment 202 comprises an internal portion 203 formed of a non-resorbable, non-shape memory material which is substantially encapsulated by an outer portion 204 formed of non-resorbable polymeric shape memory material and the second segment 201 comprises a non-resorbable, non-shape memory material. The dental post 170 illustrated in FIG. 21 additionally comprises a third segment 210, comprising a non-resorbable, non-shape memory material. The third segment 210 is positioned adjacent the second segment and the second end 14 of the root member 12.

Figure 22:
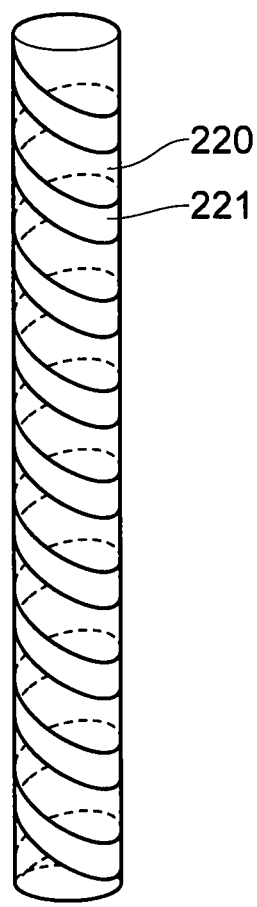

As illustrated in FIG. 22, a device 170 may comprise a body 220 comprising non-resorbable material and an elongate portion 221 comprising polymeric shape memory material. The elongate portion 221 is arranged in a coil formation around the body 220, housed within an indentation defined by the body 220.

Figure 23:
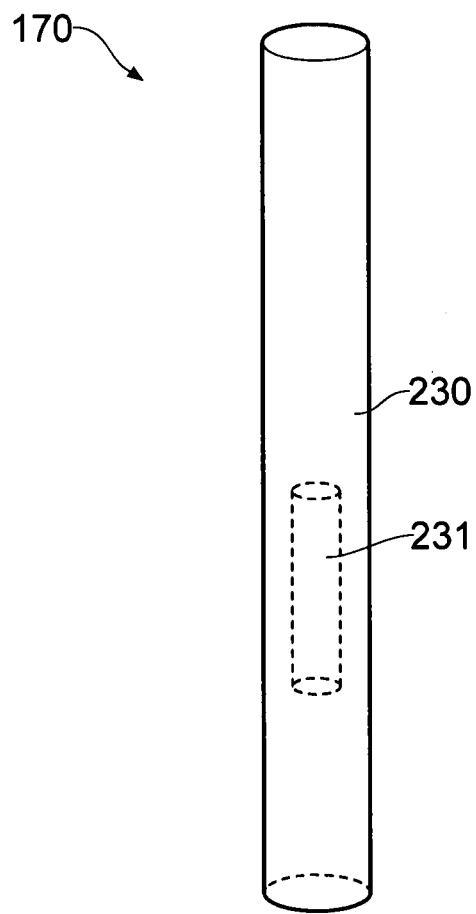

FIG. 23 illustrates a dental post 170 comprising an outer portion 230 comprising non-resorbable material and an inner portion 231 comprising polymeric shape memory material. The outer portion 230 is arranged to partially encapsulate the inner portion 231. The outer portion 230 has a substantially solid structure defining a void in which the inner portion 231 is located. The outer portion 230 defines at least one opening contiguous with the void, such that the polymeric shape memory material of the inner portion 231 can extend therethrough. Once inserted into a cavity, and upon activation, the polymeric shape-memory material of the inner portion 231 will relax, expand through the opening and anchor against the walls of the cavity.

Figure 24:
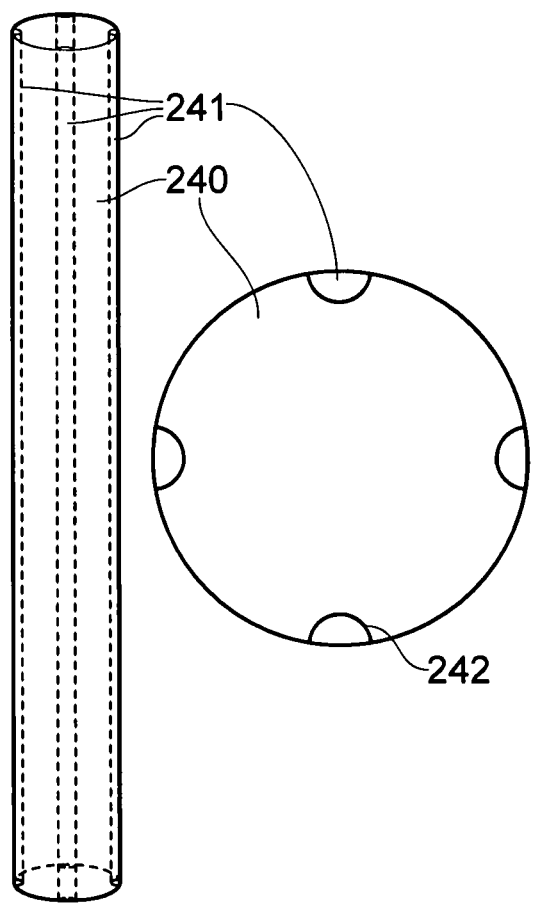

FIG. 24 illustrates a dental post 170, wherein the root member 12 comprises a body 240 comprising non-resorbable material and a plurality of elongate portions 241 comprising polymeric shape memory material. The elongate portions 241 are housed within recesses 242 in the body 240 which extend longitudinally between the first end 13 and the second end 14 of the root member 12.

It should be understood that various changes and modifications can be made to the embodiments described herein without departing from the spirit and scope of the present invention and without diminishing its attendant advantages.

The invention claimed is:

1. An implantable dental device comprising:
a root member for implantation into a cavity in either alveolar bone or a root canal space of a tooth, wherein the root member includes at least one first portion comprising a polymeric shape memory material defining a collar portion which encapsulates an internal support structure, at least one second portion comprising a non-shape memory material, and an abutment mount for receiving a dental prosthesis, wherein the collar portion defines a non-threaded outer surface extending from the at least one second portion to the abutment mount, the polymeric shape memory material is activatable from a deformed state to a relaxed state upon input of energy to the polymeric shape memory material, wherein the deformed state is sized and shaped for insertion into the cavity, wherein the relaxed state has a size and shape that is laterally expanded relative to the deformed state for sealing engagement of the non-threaded outer surface of the collar portion with an inner wall of the cavity adjacent the abutment mount to thereby anchor the root member in position and to provide a seal between the root member and the inner wall of the cavity.

2. The device of claim 1, wherein the root member is implantable as a single unit.

3. The device of claim 1, wherein the root member comprises a first end, a second end distal thereto and an outer surface which extends between the first end and the second end, wherein at least a portion of the outer surface of the root member is defined by the non-threaded outer surface of the collar portion.

4. The device of claim 1, further comprising a dental prosthesis attached to the abutment mount.

5. The device of claim 1, wherein the at least one first portion of the root member comprises a second collar portion comprising the polymeric shape memory material extending from the at least one second portion and toward a distal end of the root member.

6. The device of claim 1, wherein the non-shape memory material is a metallic material.

7. The device of claim 6, wherein the at least one second portion comprising the non-shape memory material is arranged to abut the at least one first portion comprising the polymeric shape memory material and abutment of the polymeric shape memory material with the non-shape memory material prevents longitudinal expansion of the polymeric shape memory material on relaxation and allows lateral expansion thereof.

8. The device of claim 1, wherein the non-threaded outer surface of the collar portion comprises a smooth outer surface extending from the at least one second portion to the abutment mount.

9. The device of claim 8, wherein the collar portion is positioned adjacent a first proximal end of the root member opposite a distal second end of the root member, the collar portion forming a proximal seal with the inner wall of the cavity.

10. The device of claim 1, wherein the root member comprises two or more adjoining segments, wherein at least one segment comprises the at least one first portion of the polymeric shape memory material and at least one other segment comprises a non-resorbable material, the at least one other segment comprising the at least one second portion.

11. The device of claim 1, wherein the root member comprises a plurality of adjoined segments, wherein a first population of the adjoined segments comprises the polymeric shape memory material and a second population of the adjoined segments comprises a non-resorbable material, the second population of the adjoined segments including the at least one second portion, wherein the plurality of adjoined segments are arranged in an alternating sequence along some or all of the length of the root member, and wherein the first population of the adjoined segments define a non-threaded outer surface and the second population of the adjoined segments define a threaded outer surface.

12. The device of claim 1, wherein the root member comprises a plurality of adjoined segments, wherein a first population of the adjoined segments comprises the polymeric shape memory material and a second population of the adjoined segments comprises a non-shape memory material, the second population of the adjoined segments including the at least one second portion, and wherein the plurality of adjoined segments are arranged in an alternating sequence along some or all of the length of the root member, and wherein the first population of the adjoined segments define a non-threaded outer surface and the second population of the adjoined segments define a threaded outer surface.

13. The device of claim 1, wherein at least a distal portion of the root member is formed from a single contiguous portion comprising a third portion of the root member formed of the polymeric shape memory material.

14. The device of claim 1, wherein the polymeric shape memory material comprises resorbable polymeric shape memory material.

15. The device of claim 1, wherein the polymeric shape memory material comprises non-resorbable polymeric shape memory material.

16. The device of claim 1, wherein an active agent is incorporated into the root member.

17. The device of claim 16, wherein the active agent is selected from the group consisting of bone morphogenic proteins, antibiotics, anti-inflammatories, angiogenic factors, osteogenic factors, monobutyrin, omental extracts, thrombin, modified proteins, platelet rich plasma/solution, platelet poor plasma/solution, bone marrow aspirate, and cells sourced from flora or fauna, such as living cells, preserved cells, dormant cells, and dead cells.

18. The device of claim 1, wherein the device has a generally elongate shape, a cylindrical shape or has a screw-shape.

19. The device of claim 1, wherein the root member comprises reinforced polymeric material.

20. The device of claim 1, wherein the root member comprises a combination of metal or a metal alloy and the polymeric shape memory material.

21. The device of claim 1, wherein the root member comprises porous material.

22. A kit comprising the device of claim 1 and a dental prosthesis.

23. The device of claim 1, wherein the root member comprises a first longitudinal segment having a threaded body portion comprising the at least one second portion formed of a metallic material, and the root member comprising a second longitudinal segment comprising the non-threaded collar portion formed of the polymeric shape memory material.

24. The device of claim 23, wherein the root member further comprises a third longitudinal segment comprising another of the non-threaded collar portion formed of the polymeric shape memory material, the second and third longitudinal segments arranged on opposite sides of the first longitudinal segment, the second and third longitudinal segments each having the deformed state sized and shaped for insertion into the cavity and the relaxed state having a size and shape that is laterally expanded relative to the deformed state for engagement with the inner wall of the cavity to thereby anchor the root member in position, and wherein one of the second and third longitudinal segments is positioned adjacent a first end of the root member opposite a distal second end of the root member to form an enhanced seal between the root member and the inner wall of the cavity when transitioned from the deformed state to the relaxed state.

25. The device of claim 24, wherein the non-threaded collar portion of the second and third longitudinal segments each surround an internal structure that is not formed of the polymeric shape memory material.

26. The device of claim 25, wherein the internal structure of the second and third longitudinal segments comprises a rod formed of a metallic material.

27. The device of claim 1, wherein the at least one first portion of the polymeric shape memory material expands in both an axial direction and a lateral direction when transitioned from the deformed state to the relaxed state.

28. The device of claim 27, wherein the at least one first portion of the polymeric shape memory material substantially fills a corresponding portion of the cavity when transitioned to the relaxed state.

29. A method of implantation of the implantable dental device of claim 3 into the cavity within the alveolar bone of a jaw, wherein the method comprises the steps of:
 a) drilling the cavity in the alveolar bone of the jaw,
 b) inserting the second end of the root member into the cavity, and
 c) activating the polymeric shape memory material of the root member to cause relaxation thereof, thereby fixating the root member within the cavity and forming an enhanced seal between the root member and the inner wall of the cavity adjacent the first end of the root member.

30. A method for implantation of the implantable dental device of claim 3 into the cavity within the root canal space of a tooth, wherein the method comprises the steps of:
 a) preparing the tooth by drilling the cavity in the root canal
 b) inserting the second end of the root member into the drilled cavity
 c) activating the polymeric shape memory material of the root member to cause relaxation thereof, thereby fixating the root member within the cavity and forming an enhanced seal between the root member and the inner wall of the cavity adjacent the first end of the root member.

31. An implantable dental device comprising:
 a root member for implantation into a cavity in either alveolar bone or a root canal space of a tooth, wherein the root member includes at least one first portion comprising a polymeric shape memory material defining a collar portion which encapsulates an internal support structure, at least one second portion comprising a non-shape memory material, and an abutment mount for receiving a dental prosthesis, wherein the collar portion defines a non-threaded outer surface extending from the at least one second portion to the abutment mount, the polymeric shape memory material is activatable from a deformed state to a relaxed state upon input of energy to the polymeric shape memory material, wherein the deformed state is sized and shaped for insertion into the cavity, wherein the relaxed state has a size and shape that is laterally expanded relative to the deformed state for sealing engagement of the non-threaded outer surface of the collar portion with an inner wall of the cavity adjacent the abutment mount to thereby anchor the root member in position and to provide a seal between the root member and the inner wall of the cavity, and wherein the root member comprises a first end, a second end distal thereto and an outer surface which extends between the first end and the second end, wherein the outer surface of the root member is defined by the non-threaded outer surface of the polymeric shape memory material and a threaded outer surface defined by the non-shape memory material.

32. The device of claim 31, wherein the device further comprises a dental prosthesis attached to the abutment mount.

* * * * *